United States Patent [19]
Yoon

[11] 3,989,049
[45] Nov. 2, 1976

[54] METHOD OF APPLYING AN ELASTIC RING TO AN ANATOMICAL TUBULAR STRUCTURE

[76] Inventor: In Bae Yoon, 2213 Forest Ridge Road, Timonium, Md. 21093

[22] Filed: Oct. 29, 1974

[21] Appl. No.: 518,617

Related U.S. Application Data

[62] Division of Ser. No. 383,475, July 30, 1973, Pat. No. 3,870,048.

[52] U.S. Cl. ............................ 128/326; 128/303 A; 128/325
[51] Int. Cl.² ................. A61B 17/06; A61B 17/04; A61B 17/12
[58] Field of Search ........... 128/326, 6, 303 A, 320, 128/306, 4, 2 B, 334, 325

[56] References Cited
UNITED STATES PATENTS

| | | | |
|---|---|---|---|
| 2,371,082 | 3/1945 | Vistreich | 128/325 |
| 2,942,604 | 6/1960 | Gravlee, Jr. | 128/303 |
| 3,155,094 | 11/1964 | Hamilton | 128/326 |
| 3,547,124 | 12/1970 | Fergusson | 128/303 R |
| 3,760,810 | 9/1973 | Van Hoorn | 128/326 |
| 3,763,860 | 10/1973 | Clarke | 128/334 |
| 3,820,544 | 6/1974 | Semm | 128/326 |
| 3,870,048 | 3/1975 | Yoon | 128/326 |

*Primary Examiner*—Aldrich F. Medbery
*Attorney, Agent, or Firm*—Stewart and Kolasch, Ltd.

[57] ABSTRACT

A ring applicator device for use in applying an elastic occluding ring to an anatomical tubular structure which comprises an inner cylinder slidably disposed within an outer cylinder, forceps means slidably disposed within said inner cylinder, means for moving said forceps means into and out of the inner cylinder and means for ejecting an elastic ring from the end of said inner cylinder by axially displacing said outer and inner cylinders relative to each other.

23 Claims, 39 Drawing Figures

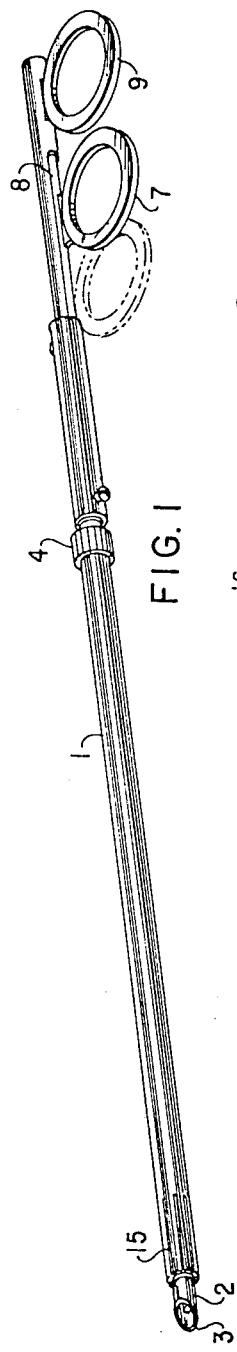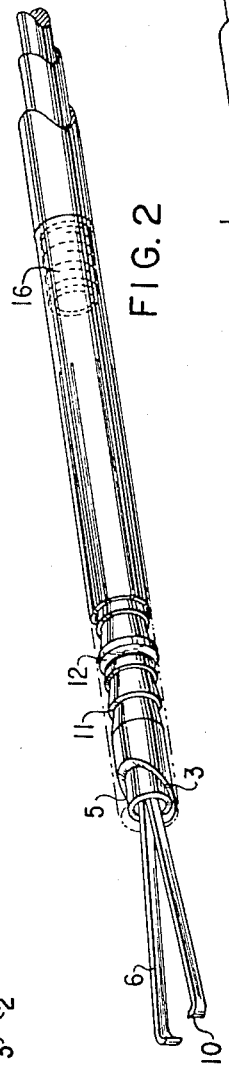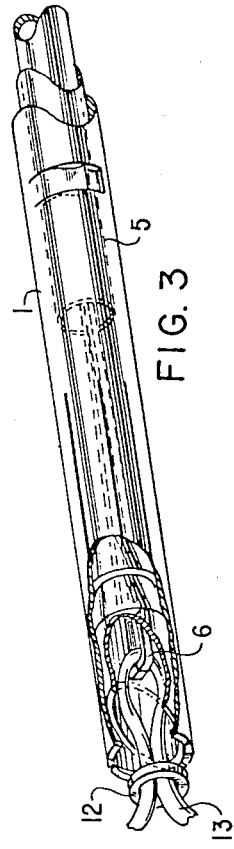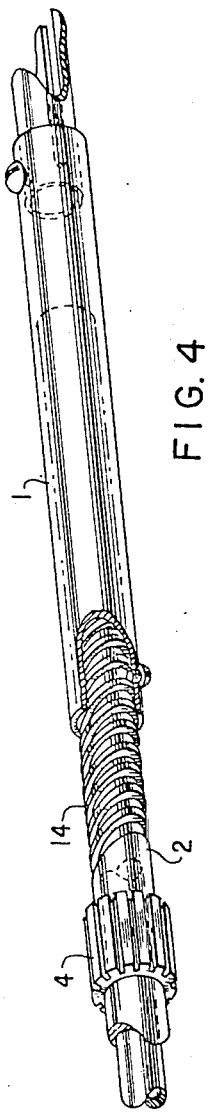

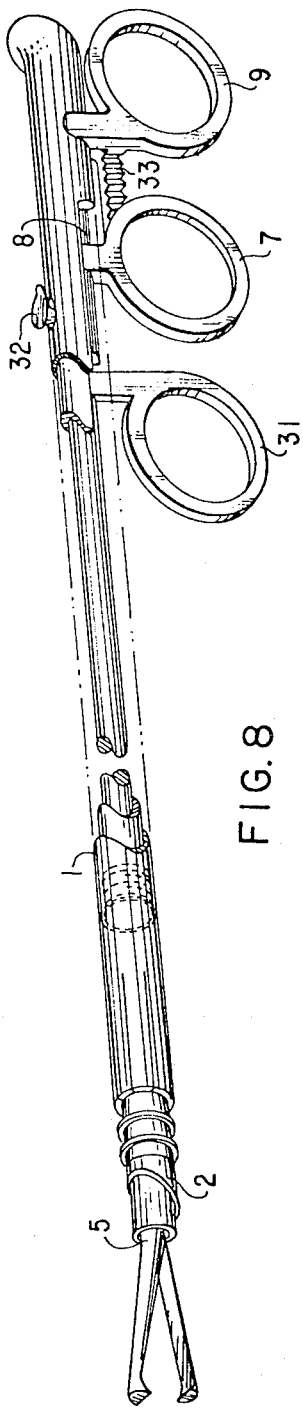
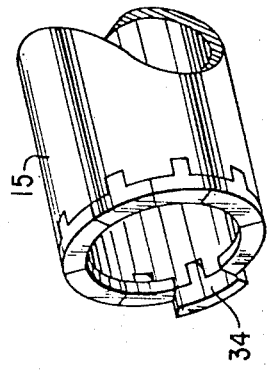

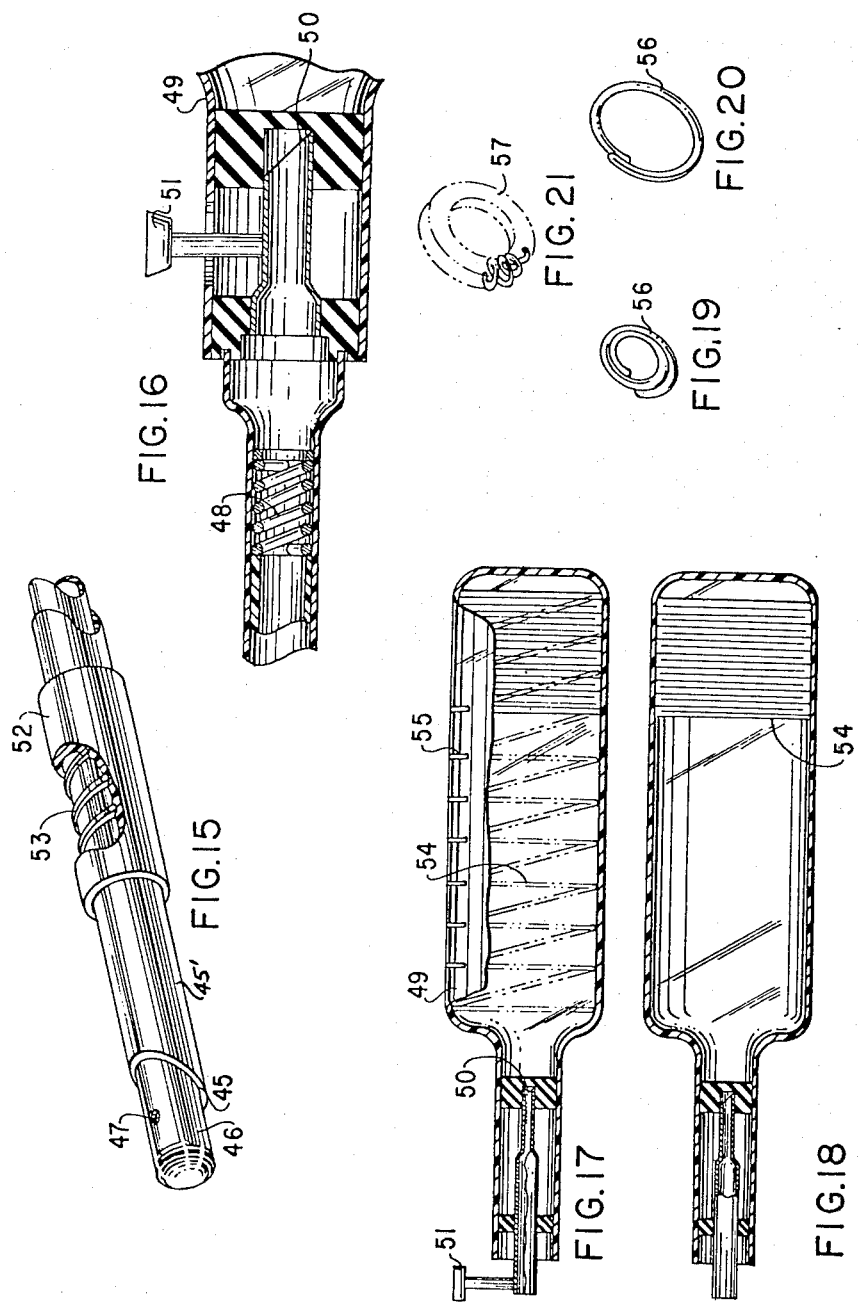

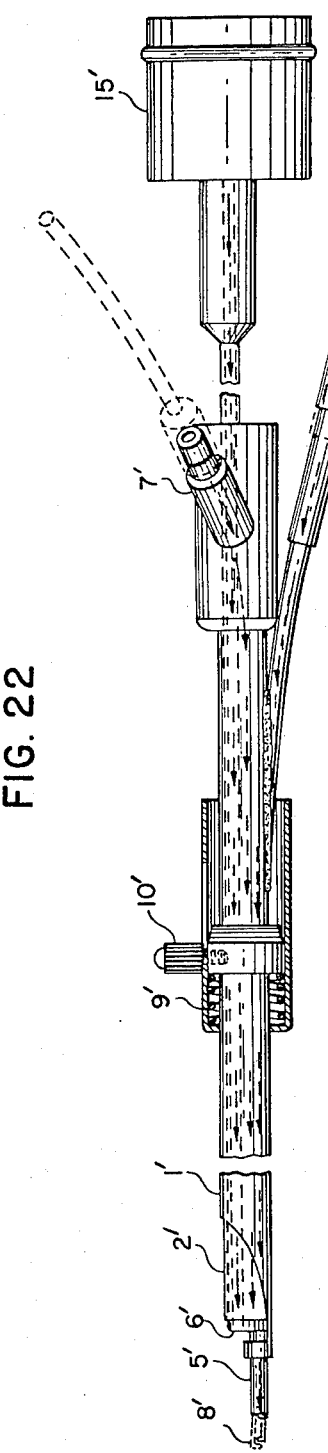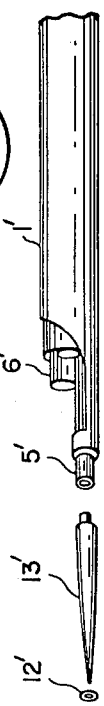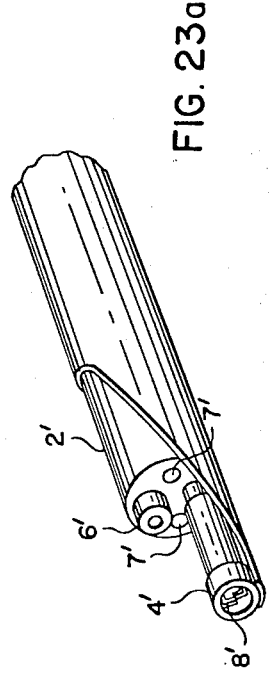
FIG. 22
FIG. 23a
FIG. 23b
FIG. 23c
FIG. 24

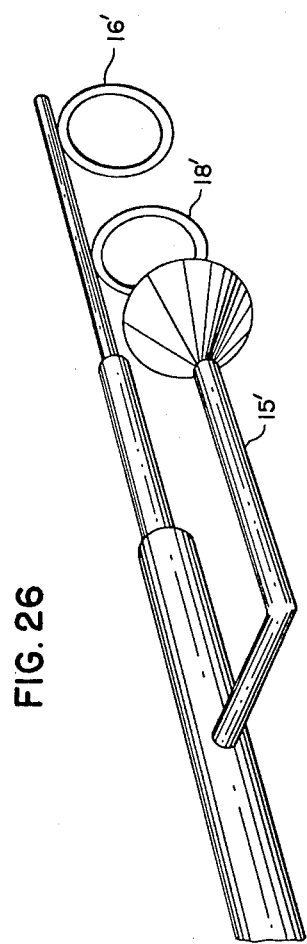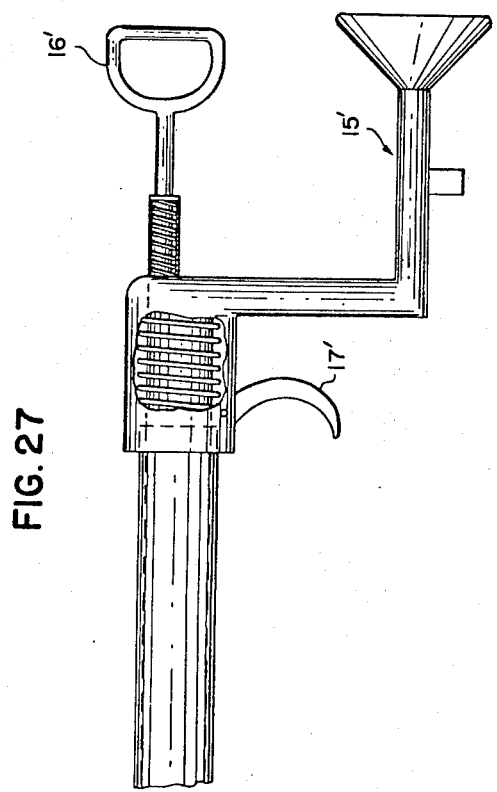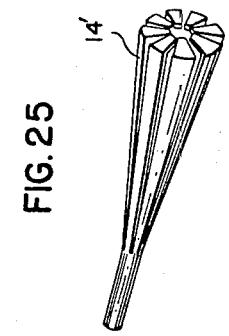

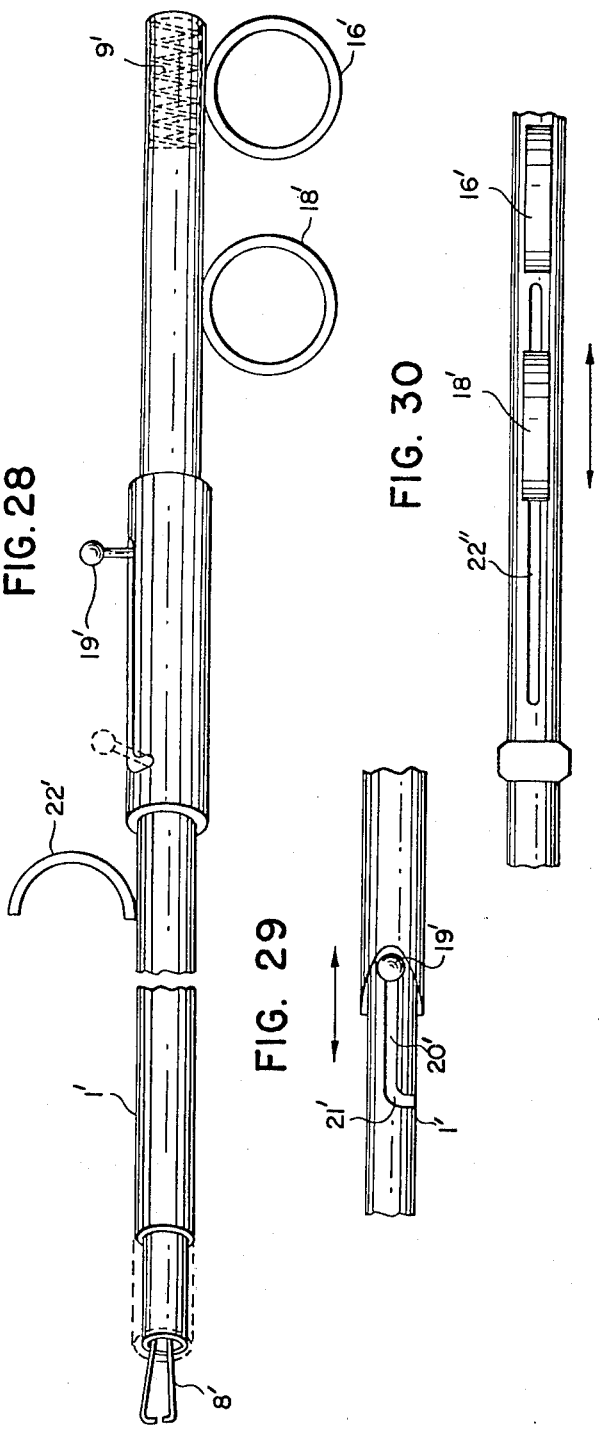

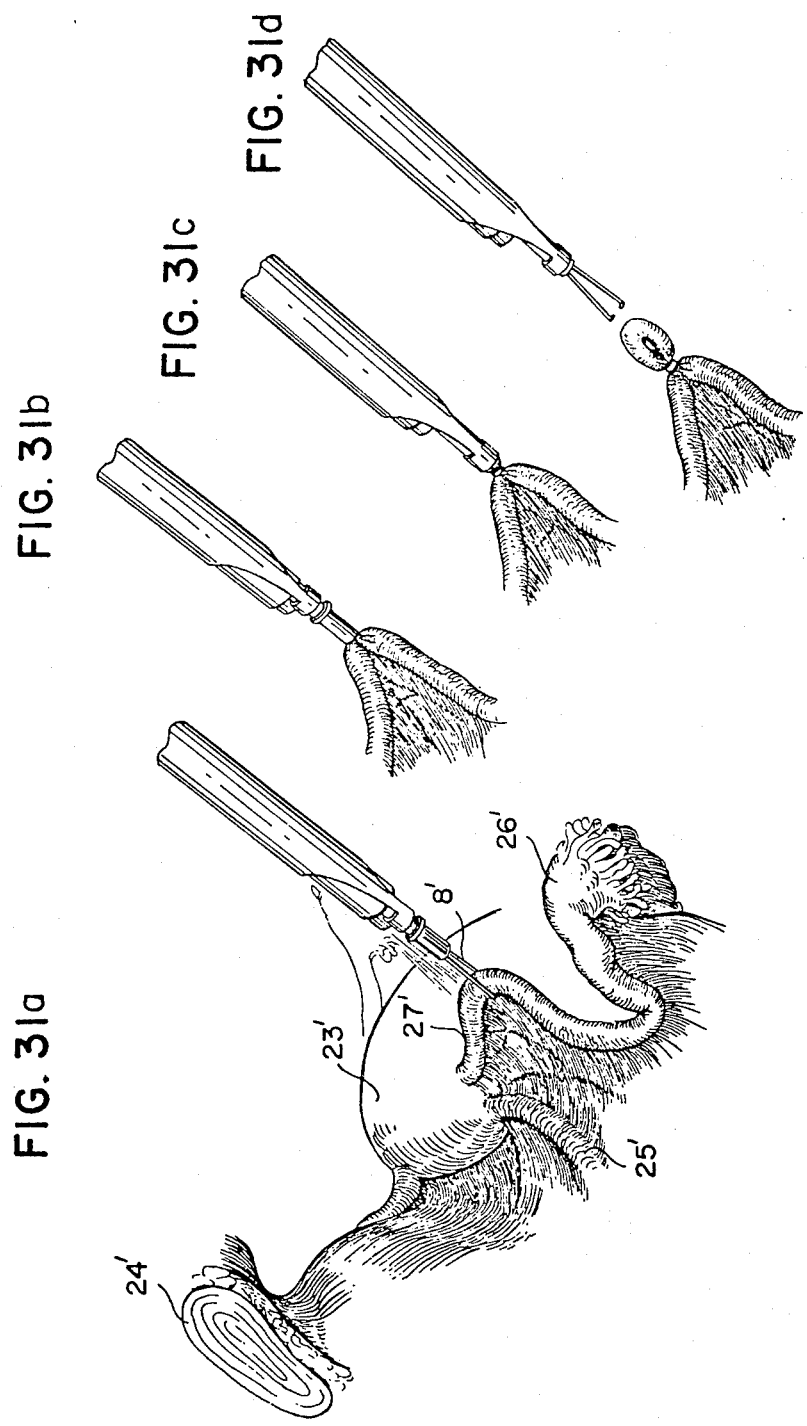

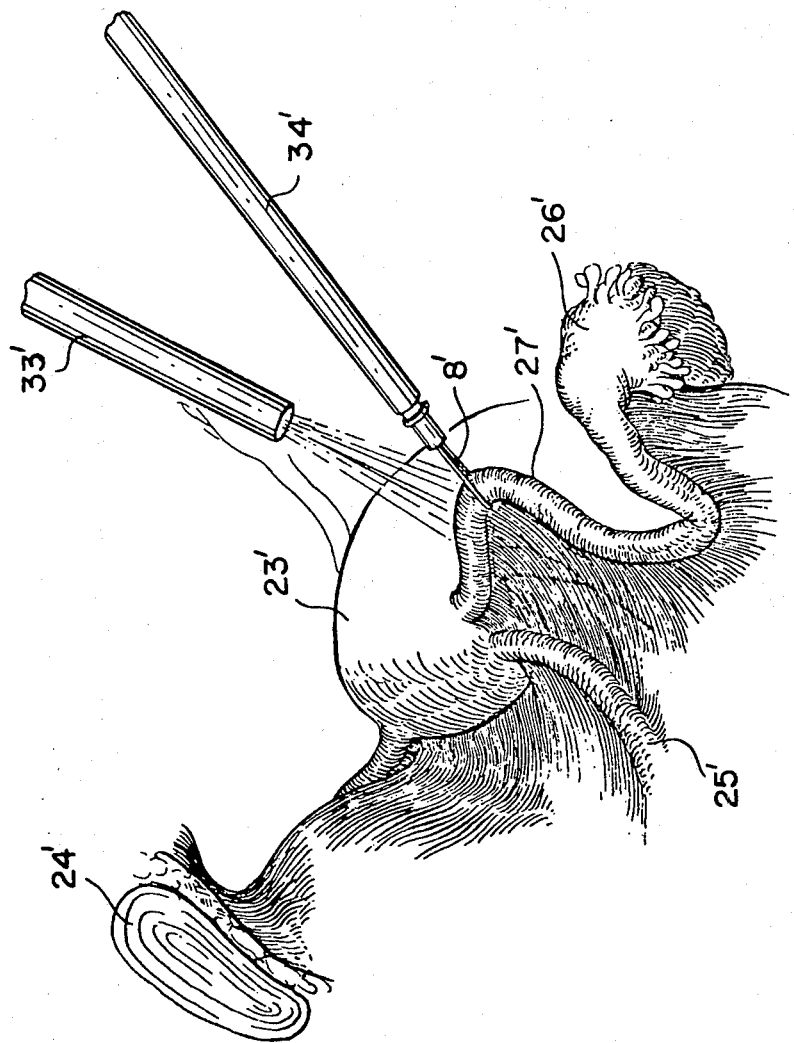

METHOD OF APPLYING AN ELASTIC RING TO AN ANATOMICAL TUBULAR STRUCTURE

The present application is a Divisional of Application Ser. No. 383,475, filed July 30, 1973, now U.S. Pat. No. 3,870,048

BACKGROUND OF THE INVENTION

The present invention relates to an occlusion ring and the method and device for applying said ring to an anatomical tubular structure. More particularly, the present invention is directed to a ring applicator device, combinations of said device with other instruments and a technique and method for carrying out tubal ligation of the human female in order to effect permanent or temporary sterilization. The device of the present invention can also be effectively used to sterilize the human male.

In many areas of the world, the question of population control has become a central issue. Since birth control devices are not always used faithfully or fail to work in some instances, various procedures have been proposed for effecting the sterilization of women as well as men. However, many of these techniques are unpopular because of the resulting complications, the high expense and because of the general unacceptability among the populace of effecting a sterilization which is permanent and cannot be reversed. Nevertheless, sterilization is obviously an effective means for solving various problems of population explosion and of voluntarily limiting the size of the family where desired on the part of the parent. Accordingly, research into finding various techniques and instruments has continued both under private and government support.

Tubal ligation has commonly been used to effect sterilization in women. The common practice is to cut and tie the Fallopian tubes in order to prevent fertilization of the egg. More recently the use of clips for closing the tubes has been suggested. Another recent procedure involves cauterization of the tubes by electrical means. However, each of these procedures involves much discomfort to the patient and highly skilled personnel to successfully complete the operation. Also, in the procedure requiring the use of clips, in some instances the clips have fallen off thereby rendering the sterilization ineffective. With respect to cauterization by means of electricity, there remains the ever present dangers of inadvertently burning certain organs of the body and, for example, accidentally rupturing the bowel.

SUMMARY OF THE INVENTION

One of the objects of the present invention is to provide a simplified instrument and method for applying an occlusion ring to an anatomical tubular structure.

Another object of the present invention is to provide a simplified instrument and method for effecting permanent or temporary sterilization of the human female.

A further object of the present invention is to provide a novel technique and instrument for accomplishing tubal ligation which may be employed by physicians with many degrees of skill and without the need for expensive or bulky equipment.

A still further object of the present invention is to provide a portable instrument for mechanically effecting tubal ligation wherein a sliding ring handle which is operatively connected to a grasping means is so disposed as to indicate to the physician the precise time when the elastic ring should be applied to the crimped Fallopian tube.

An additional further object of the present invention is to provide an applicator device which is physically combined with a laparoscope system in such a way as to enable the physician operating the device to view the entire ligation operation.

An additional further object of the present invention is to provide an applicator device which is physically combined with a laparoscope system in such a way as to enable the physician operating the device to view the entire ligation operation.

Yet another object of the present invention is to provide a laparoscope which is combined with a ring applicator device in such a manner as to substantially eliminate the contamination of the instrument or the physician's hand.

Still another object of the present invention is to provide an instrument which can also be used for the sterilization of the human male.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

Pursuant to the present invention, the above-mentioned disadvantages may be eliminated and an improved ligature method and ring applicator device as well as a combination of said device with a laparoscopic system may be obtained by following the teachings of the ring applicator device of the present invention.

In accordance with the present invention, the sterilization of the human female or human male may be attained by the use of elastic rings for effecting the ligature of the Fallopian tubes. Advantageously, the ligature is performed in conjunction with a laparoscope which is an instrument well known in the medical field for viewing the internal portions of the body. The instrument of the present invention is a ring applicator which is used to quickly and effectively slip a small elastic or rubbery ring around the Fallopian tubes of the female in order to permanently or temporarily block the same. Basically, the instrument of the present invention, shown in detail in the attached drawings, includes a grasping means which is used to pull a portion of the Fallopian tube of the female into the device and slidable or rotatable tubular means for slipping or pushing the elastic or stretchable ring over the portion of the Fallopian tube held in the device, thereby effecting the ligature. In operation, the entire device is inserted through the abdominal wall or by means of the vaginal route, the grasping means is pushed forward to engage a sigment of the Fallopian tube, the grasping means is then retracted into the inner tube of the applicator device, and finally the device is manipulated so as to release the elastic ring from the end of the applicator and place it around the segment of the Fallopian tube contained therein. Thereafter, the loop held by the elastic ring can be cut by the grasping means for permanent sterilization, if desired, or the loop can be left as is with the elastic ring holding the Fallopian tube in a crimped position thereby permanently or temporarily effecting sterilization. Temporary sterilization is contemplated by cutting the elastic band in a subsequent operative procedure.

When the applicator device is used in conjunction with a laparoscope, a very small incision may be made when using either the abdominal or vaginal approach because the light associated with the laparoscope facilitates the location of the Fallopian tubes. However, when the ring applicator device is used without the aid of a laparoscope, a slightly larger incision is required in order for the physician to locate the Fallopian tubes.

BRIEF DESCRIPTION OF THE DRAWINGS

The present invention will become more fully understood from the detailed description given hereinbelow and the accompanying drawings which are given by way of illustration only, and thus are not limitative of the present invention and wherein, FIG. 1–4 show the operation of one embodiment of the ring applicator of the present invention;

FIG. 8 shows another embodiment of the ring applicator of the present invention;

FIG. 9 shows another embodiment of the front end portion of the ring applicator which is used to eject the elastic rings from the end of said applicator;

FIG. 10 discloses an embodiment in which a cannula, a laparoscope and the ring applicator can be used in an effective combination;

FIGS. 15 and 16 show the front and rear end portions, respectively, of a device for introducing a gas into the body cavity;

FIGS. 17 and 18 disclose a further view of the rear end portion of the device of FIG. 16 where the gas cylinder is shown in the loaded and unloaded position;

FIGS. 19, 20 and 21, show enlarged views of stainless steel type rings which can be used in place of the elastic rings with the device;

FIG. 22 shows another embodiment of the ring applicator device of the present invention in combination with a laparoscope;

FIGS. 23a, 23b and 23c show the loading device which can be inserted into the front end of the ring applicator device for loading the elastic rings onto the end of said ring applicator device;

FIG. 24 shows, in greater detail, the front end portion of the ring applicator device and the positioning of the laparoscope relative to the grasping means of the ring applicator device of FIG. 22;

FIG. 25 shows the pusher device which is utilized to push the ring from the loading device onto the end of the ring applicator device;

FIG. 26 shows another embodiment of the present invention wherein a portion of the laparoscope is offset with respect to the ring applicator device;

FIG. 27 shows another embodiment of the present invention wherein a trigger means is utilized for applying the elastic ring to the Fallopian tube;

FIG. 28 shows another embodiment of the present invention wherein an improved ring applicator device is used not in combination with a laparoscope;

FIG. 29 shows a top view of a lever and the guide slot used by said lever in pushing the inside cylinder of the ring applicator of FIG. 28 to the forward position;

FIG. 30 shows the bottom view of the sliding handle ring which slides back and forth in a slot to expel and retract the grasping means;

FIGS. 31a, 31b, 31c and 31d show in sequential steps, the abdominal method of performing the ligation of the Fallopian tube using the ring applicator device of the present invention in combination with the laparoscope wherein the device is inserted through the abdominal wall by a single incision made in the navel area;

FIG. 32 shows the abdominal method using the two hole technique wherein the culdoscope (light source) and the ring applicator are inserted through the abdominal wall through two separate incisions;

DETAILED DESCRIPTION OF THE DRAWINGS

Figure 5:
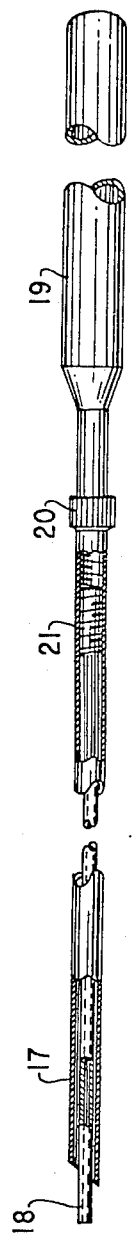
FIG. 5 discloses a needle like instrument for introducing a gas into the body cavity.

One embodiment of the ring applicator of the present invention is shown in FIGS. 1 to 4. The device comprises an inner tube 2 disposed within an outer tube 1, said inner tube being provided with a cutting edge 3 at its front end. The outer tube is in engaging relationship with the inner tube so that by rotating the outer tube using gripping means 4 said outer tube is moved axially in the direction of the cutting edge 3. Grasping means 5 which is provided at one end with forceps 6 and at the other end with a sliding ring 7 is slidably disposed within the inner tube 2. By manually moving the sliding ring 7 the forceps 6 can be moved into and out of the inner tube 2. For example, by moving sliding ring 7 in the direction indicated in FIG. 1 along groove 8, relating to the stationary ring 9, the forceps 6 which is compressed within tube 2, as shown in FIG. 1, is pushed out of the end portion of said tube to a position shown in FIG. 2, the arms of said forceps springing apart because of their inherent resiliency or spring-like property. If desired, the forceps means can be provided with cutting edges 10. The stationary ring 9 is provided to facilitate grasping the ring applicator and sliding the ring 7. The front end portion of tube 2 is provided with a plurality of grooves 11 which are adapted to receive elastic rings 12.

FIG. 3 shows the position of the ring applicator at a time when, for example, the tube 13 of the female is grasped by the forceps 6 and pulled inside tube 2. By turning the outer tube 1 about the external thread 14 provided on inner tube 2, the end portion 15, which can be made, for example, of spring metal, pushes the end elastic ring from the tube 2 to a position around the crimped tube 13. Then by reversing the direction of the grasping means 5, the forceps is pushed from the tube 2 which causes it to spring open, releasing the tube 13 held in a crimped condition by the elastic ring. By reversing the direction of the outer tube 1 using gripping means 4, the spring nature of the end portion 15 of said outer tube causes said portion to enlarge around the end elastic ring 12 and position itself therebehind. The device is now loaded again and in a position to discharge a second elastic ring. It is to be understood that a plurality of elastic rings may be provided in the grooves 11 of tube 2 so that one ring at a time can be used, as desired by the physician. The end portion 15 of the outer tube 1 can be attached to tube 1 by screw means 16.

FIG. 4 indicates one location in which screw threads 14 can be utilized to effect the movement of tube 1 relative to tube 2. The screw threads may, of course, be provided at any convenient location between said tubes. Also, the gripping means 4 can be provided at any convenient location.

FIG. 5 illustrates a needle instrument which is used to puncture the body cavity as the first step in the operational procedure. This instrument comprises a thin cylinder 17 which acts as a needle to puncture the skin. The needle surrounds blunted stylet 18 which functions to introduce a gas, e.g., carbon dioxide, from container 19 into the abdominal cavity. Gripping means 20 is used to rotate cylinder 17 with respect to stylet 18, said stylet being provided with external threads 21. Thus, the gas is introduced into the body through the end hole in stylet 18 as it protrudes beyond the end of cylinder-needle 17.

Figure 6:
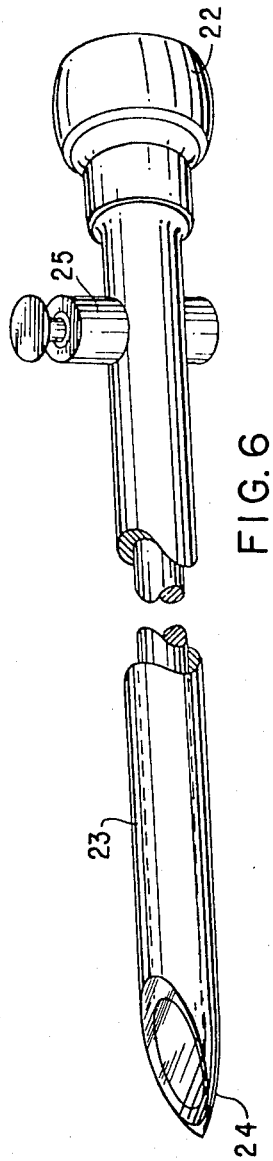
FIG. 6 shows a cannula with a trocar associated therewith to facilitate entry of the ring applicator into the body cavity; m

After inflating the body cavity with carbon dioxide gas, a trocar 22, shown in FIG. 6, with a cannula 23 is introduced into the body by umbilical incision. The trocar has a pointed end 24, thereby permitting easy entry through the skin. The trocar is removed and the cannula is left in position to hold the ring applicator and/or laparoscope for use as discussed below. As can be noted in FIG. 6, the cannula is provided with a valve, e.g., a trumpet valve 25, to prevent the carbon dioxide gas from escaping.

Figure 7:
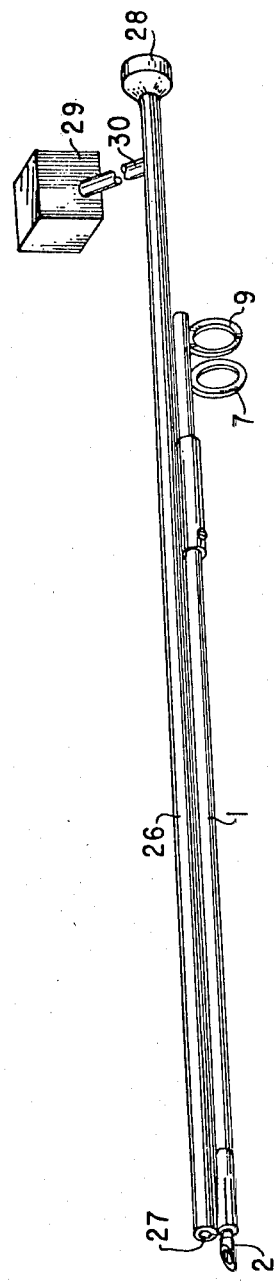
FIG. 7 shows the ring applicator of FIGS. 1 to 4 used in combination with a laparoscope.

Laparoscopy is a well known and widely accepted technique in the medical field at the present time. The ring applicator of the present invention can be used in conjunction with a laparoscope as is schematically shown in FIG. 7, or it can be used as part of a two-hole technique using the cannula-trocar arrangement shown in FIG. 10. In FIG. 7, the ring applicator of the invention, for example, the instrument of FIG. 1, is attached to laparoscope 26. Laparoscope 26 is used to view the internal cavity during the operation by viewing through lenses 27 and 28. Light source 29 introduces a light into channel 30 to the instrument to facilitate viewing. The two instruments need not be attached, and a trocar containing two holes, as shown in FIG. 10, can be used to permit entry of the ring applicator and the laparoscope into the abdominal cavity. Alternatively, the ring applicator device of the invention can be used in conjunction with a culdoscope when entry is made through the vaginal cavity.

FIG. 8 shows another embodiment of the present invention wherein tubes 1 and 2 are slidably disposed with respect to each other and thus tube 2 is slid into and out of tube 1 by sliding ring 7 along groove 8. This is to be compared with the embodiment of FIG. 1 wherein screw threads are provided to enable the movement of tubes 1 and 2 with respect to each other. Also in this embodiment, ring 31 is utilized to slide grasping means 5 into and out of inner tube 2. In one feature of the present invention, a locking device 32 may be provided to lock the inner and outer tubes with respect to each other. The specific location of the locking device, as shown, facilitates locking tubes 1 and 2 together with the physician's same hand. Alternatively, a locking device in the form of a ratchet means 33 can also be used not only as an equivalent type locking device, but also to enable the axial movement of the tubes, relative to each other, in predetermined increments.

FIG. 9 shows another embodiment of the front end portion 15 of the outer tube 1. Thus, said front end portion 15 can be provided with a plurality of spring-loaded sections 34 which are forced open by the elastic ring disposed on the inner tube 2 when the inner tube 2 is pulled inside the outer tube 1. Thus, for example, when the ring applicator is ready for use, the grooves 11 are loaded with elastic rings 12 and the front end portion 15 of the outer tube 1 extends over all of the elastic rings except the end ring which is to be first used during the operational procedure. By sliding inner tube 2 into outer tube 1, the elastic ring is pushed from the end of the applicator onto the crimped female tube. Then by sliding tube 2 out of tube 1, the enlarged diameter of the elastic ring disposed around the inner tube forces the spring loaded sections 34 open until said sections have reached a position between adjacent elastic rings, at which point section 34 springs closed, leaving an exposed elastic ring for next use and housing the remaining elastic rings.

FIG. 10 is similar to FIG. 6 with the exception that two trocars 22 are utilized so that multiple instruments can be used simultaneously. Also FIG. 10 shows the use of a screw-type surface 35 on the outer surface of the cannula to facilitate the introduction of the cannula into the body cavity and to prevent accidental rupturing.

Figure 11:
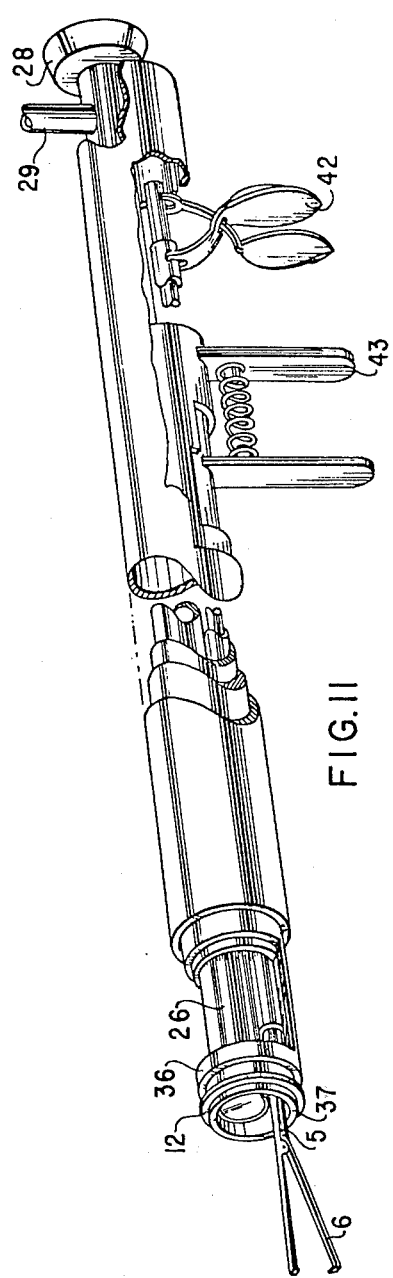
FIG. 11 shows another embodiment of the ring applicator of the present invention in combination with a laparoscope.
Figure 13:
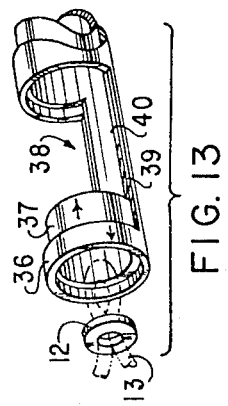
FIG. 13 shows how the front end portions of FIG. 11 slide with respect to each other to mount the elastic ring on the tube.
Figure 12:
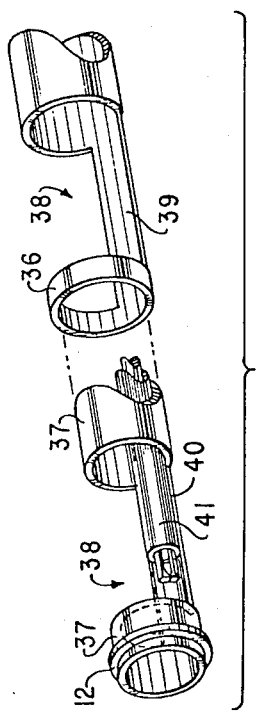
FIG. 12 shows the front end portion of the combination shown in FIG. 11.

FIGS. 11, 12 and 13 illustrate still another embodiment of the present invention showing a laparoscope and a ring applicator device used in combination. Also a means (not shown) can be provided for introducing a gas into the body cavity between concentric tubes. In said FIGS., an inner tube 37 is slidably disposed within an outer tube 36, both of said tubes having a cut-away portion 38, so that the front and rear portions of tubes 36 and 37 are connected by saddle portions 39 and 40. Portions of tubes 36 and 37 are cutaway to provide the physician with a better overall view when looking axially through the laparoscope. An additional tube or conduit 41 is cradled in the bottom portion of the inner tube 37, said tube housing the grasping means 5 which can be moved into and out of said tube. Squeeze handles 42 operate to open and close the forceps 6. In this embodiment, one of the forceps arms is rigid and the other one is hinged with respect thereto so that the forceps can be opened and closed by the operation of said squeeze handles. Also squeeze handles 43 are associated with tubes 36 and 37 so that said tubes can be moved relative to each other, said movement pushing the elastic ring 12 from the end of tube 37 by tube 36. The embodiment of FIGS. 11, 12 and 13 is also provided with a light source 29 for the laparoscope and an air bulb or carbon dioxide source (not shown) can be introduced between concentric tubes into the body cavity.

Figure 14:
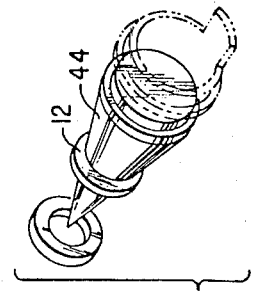
FIG. 14 shows a device for loading the elastic rings onto the end portion of a ring applicator.

FIG. 14 shows a cone-shaped ring applicator 44 for applying the elastic rings to the end of the tubes.

FIGS. 15 and 16 show cutaway views of the front and rear end portions respectively of a needle instrument for injecting a gas into the body cavity. The front portion shows a cutting edge 45 and a hollow rod 46 with a hole 47. The hollow rod 46 which is spring loaded by spring 48 provides communication between the body cavity and a carbon dioxide cannister 49. Thus, after the body cavity is cut or punctured by the cutting edge 45, the spring 48 pushes the hollow rod 46 into the body cavity thereby exposing hole 47 to said cavity. Then by pushing the cutting edge 50 into the carbon dioxide cannister 49, the gas is conveyed under a positive pressure from the cannister through the hole 47 into said body cavity. The cutting edge 50 can be provided with a gauge handle 51 which enables the operator to insert or retract the cutting edge in a controlled manner, thereby controlling the introduction of carbon dioxide into the body cavity.

The needle in FIG. 15 is also shown as containing a sleeve 52 which is internally threaded to receive external threads 53 provided on needle body 45'. The sleeve, which does not enter the body cavity but rather abuts against the outside of the body, e.g., the abdomen, functions to prevent the needle from being pushed into the body in an uncontrolled fashion. Thus the rod can be screwed into the body in increments in a controlled manner. This advantageous feature avoids the undesired penetration of other organs. It is apparent that such a screw arrangement can be adopted to the introduction of any instrument into the body.

FIGS. 17 and 18 show how the gas in the cannister 49 is maintained under pressure. In FIG. 17, a collapsible type baffle arrangement 54 pushes forward to assist the movement of the gas from the cannister into the needle instrument. FIG. 18 shows a cannister loaded with a gas inasmuch as the baffle means 54 is compressed against the rear portion of the cannister. Hence, a positive pressure is then present in cannister 49. The cannister can also be provided with a gauge 55 for visually determining the amount of gas which has been removed from the cannister. The cannister 49 can be made to be rechargeable by providing a valve (not shown) for reintroducing the gas therein.

FIGS. 19 and 20 show a spring stainless steel metal ring which can be used in place of the elastic rings. In FIG. 20 the ring is shown as it would appear on the ring applicator in an extended condition and FIG. 19 shows how it would appear when coiled around the female tube.

FIG. 21 shows another embodiment wherein a coiled spring 57 is used in place of the elastic ring.

In practice, the operation of the present invention is conducted as follows. First, a needle-like instrument of the type described above is inserted into the navel area in order to permit the flow of carbon dioxide or air into the abdominal cavity so as to provide more space within which to work inside the cavity. After the appropriate amount of gas has been introduced, the needle-like instrument is removed and is replaced by the trocar-cannula combination. If the operation is being performed with the ring applicator of the invention being separate from the laparoscope, the single trocar is removed and replaced with said ring applicator. A laparoscope is inserted into the abdominal cavity for viewing purposes at a different location. In the case where two-hole laparoscopy is being employed, a cannula containing two trocars is employed, and the ring applicator of the invention is placed into one of these holes and the laparoscope into the other of these holes. In this case, the ring applicator and the laparoscope can both be operated by the same physician.

After positioning the instruments properly within the body with the aid of the view provided by the laparoscope, the physician engages the Fallopian tube in the forceps means, pulls the tube inside of the ring applicator instrument and then slips the elastic band over the tube. The forceps means is then ejected from the instrument and the tube disengaged therefrom. If desired, two or more rings may be placed upon either or both of the tubes. The instruments are then removed, the cannula is removed and appropriate measures are used to insure that the incision or small hole in the skin area is properly cared for.

Another embodiment of the ring applicator of the present invention is shown in FIG. 22. The device comprises an inner cylinder 2' disposed within an outer cylinder 1' said inner cylinder being slidably engaged with said outer cylinder. Thus, the outer cylinder 1' can be axially moved relative to the inner cylinder 2'. The outer cylinder is provided with a ring pusher 4' which is in sliding relationship with hollow cylinder 5'. The inner cylinder 2' houses a laproscope 6', a light source 7', for example fiber optics, disposed on both sides of the laparoscope and cylinder 5'which is adapted to house the grasping means 8'. In operation, the outer cylinder 1' is pushed in the backward direction against the action of the spring 9' and locked in the position shown in FIG. 22 by the screw lock 10'. The ring applicator device is now ready to be loaded with the elastic band 12'. Referring now to FIGS. 23a, 23b and 23c, the elastic ring is inserted with the fingers onto the end of the loading device 13'. The loading device is then inserted into the end of cylinder 5' and with the aid of the expandable pushing device 14', the ring 12' is pushed along the surfce of the loading device 13' until it is loaded onto the outer surface of the cylinder 5'. In this connection, it should be noted that the pushing device 14' is segmented and made of an expandable material, for example, spring metal or an expandable plastic material which is capable of expanding as the ring is pushed along the ever increasing diameter of the loading device 13'. Once the ring 12' has been loaded on the cylinder 5', the pusher device 14' is retracted and the loading device 13' is removed from the end of cylinder 5'.

The loaded ring applicator device is now inserted into a cannula which had been previously inserted into the patient in a well known manner. By looking through the eye piece 15' of the laparoscope 6' and through the use of the light source 7' introduced into the applicator device the physician can readily see the pelvic cavity. When the Fallopian tube is discovered by the physician, the grasping forceps 8' are pushed forward utilizing the fixed ring 16' as leverage and pushing the slidable ring 18' forward until its forward movement is limited by the end of the slot 22''. The grasping forceps 8' now extend from the end of the cylinder 5'. The forceps 8' are then used to grab the Fallopian tube and pull it inside of cylinder 5'. This is accomplished by pulling the sliding ring 18' rearward until it strikes the rear end of the slot 20'. The Fallopian tube is now in a proper crimped position within the cylinder 5'. Then the locking device 10' is unscrewed thereby enabling the spring 9' to force the outer cylinder 1' in the forward direction, the nose 4' of said outer cylinder pushing the elastic band around the Fallopian tube inside of cylinder 5'. Then the ring 18' is then pushed in the forward direction thereby expelling the Fallopian tube crimped by the elastic ring from the end of the ring applicator device. The above process is repeated in order to apply the same technique to the second Fallopian tube in the same manner. The ring applicator device can then be removed from the cannula and after the cannula is removed from the patient the incision can be closed in a well known manner.

FIG. 26 shows the embodiment of the present invention wherein the laparoscope is offset from the device to permit freedom of movement of the sliding ring 18' while at the same time avoiding possible contamination by contact of the hand operating the sliding ring with the face of the physician.

FIG. 27 shows another embodiment of the present invention wherein the movement of the outer cylinder 1' with respect to the inner cylinder 2' can be accomplished by trigger action utilizing trigger means 17'. In this embodiment, while the trigger 17'is depressed, the outside cylinder 1 is pushed in the rearward direction and then the trigger is released locking the outside cylinder in said position. Now the front end of the ring applicator device is ready for loading. After the elastic ring has been loaded onto the front end of the ring applicator device and the Fallopian tube has been pulled into the cylinder 5', the elastic band can be applied to or shot onto the crimped Fallopian tube by pulling the trigger 17'. The obvious advantages of the use of the trigger device reside in simplifying the overall operation of the ring applicator for the benefit of the physician. FIG. 27 also shows the use of a single sliding ring means 16' wherein the distance the grasping means is extended from or retracted into the ring applicator is variable depending on the physician operating the device.

FIG. 28 shows one of the features of the present invention wherein the ring applicator device is shown not in combination with a laparoscope system. The use of the ring applicator device as shown in FIG. 28 without the assistance of a laparoscope requires a slightly larger incision so that the operating physician can locate the Fallopian tubes without the aid of a light source. The ring applicator device of FIG. 28 comprises an inner cylinder tube 2' coaxially and slidably disposed within an outer cylinder 1'. The outer cylinder 1' is provided with a handle means 22'to aid the physician in stabilizing the instrument during the operative procedure. The inner tube 2' is associated with a spring 9' such that when the lever 19' is pushed in the forward direction along slot 20 and locked in section 21' of slot 20', the inner cylinder 2' is pushed forward and extends beyond the front end of the outer cylinder 1' as shown in FIG. 7'. Now the front end of the ring applicator device can be loaded with the elastic band 12' in the manner described above. With the ring applicator in the loaded state it is inserted into the patient through a cannula in a known manner and upon the location of the Fallopian tube the ring 18' which is attached to forceps 8' disposed inside of the cylinder 2' is pushed forward in slot 20' until said forceps extend beyond the front portion of cylinder 2'. The extent to which the ring 8'is pushed in the forward direction is limited by the length of the slot 20' shown in FIG. 9'. Upon grasping the Fallopian tube with the forceps 8', the ring 18' is pulled in the reverse direction drawing the Fallopian tube in a crimped position inside of cylinder 2'. Because the ring 16' is fixed, when the ring 18 is pulled into contact with ring 16', which is also at the end of the slot 20', the physician knows that the Fallopian tube has, in fact, been pulled into the inner cylinder 2'. This advantageous feature addes an element of control to the ring applicator device in that the physician does not have to rely upon his judgment to determine whether or not the Fallopian tube is in the proper position for the application of the elastic band thereto. Once the ring 18' is in contact with the ring 16', which indicates that the Fallopian tube is in a proper position within cylinder 2', the lever 19' which is locked in position 21' of the slot 20' is released enabling spring 9' which has been in an extended position to pull the inner cylinder 2' in the rearward direction. In so doing, the elastic band 12' disposed on the end of the inner cylinder 2' is pushed from said tube onto the Fallopian tube by the outer cylinder 1. Now the ring 18' is pushed in the forward direction, thereby releasing the Fallopian tube containing the elastic band securely attached thereto. Of course, the above procedure is repeated with respect to the second Fallopian tube.

It can be readily understood that the use of a fixed and sliding ring in conjunction with the ring applicator device as shown in FIG. 28 is the same as that utilized in FIGS. 22 and 27 of the present application.

FIGS. 31a, 31b, 31c and 31d show, in sequence, the application of an elastic ring to a Fallopin tube using the single incision abdominal approach and utilizing the device shown in FIG. 22. In said FIGS., 23' is the uterus, 24' is the pelvic bone, 25' is a round ligament, 26' is fimbrea and 27' is the Fallopian tube. In FIG. 31a, the Fallopian tube has been grasped by the grasping means 8'. In FIG. 31b, the Fallopian tube has been pulled inside of cylinder 5'. FIG. 31c shows the elastic ring in position on the Fallopina tube and FIG. 31d shows the removal of the crimped Fallopian tube from the end of the ring applicator device. Because of the recessed position of the laparoscope, the physician can view the entire operative procedure.

FIG. 32 shows the double incision abdominal approach wherein the culdoscope and the ring applicator are inserted through separate incisions made in the abdominal wall.

Figure 33:
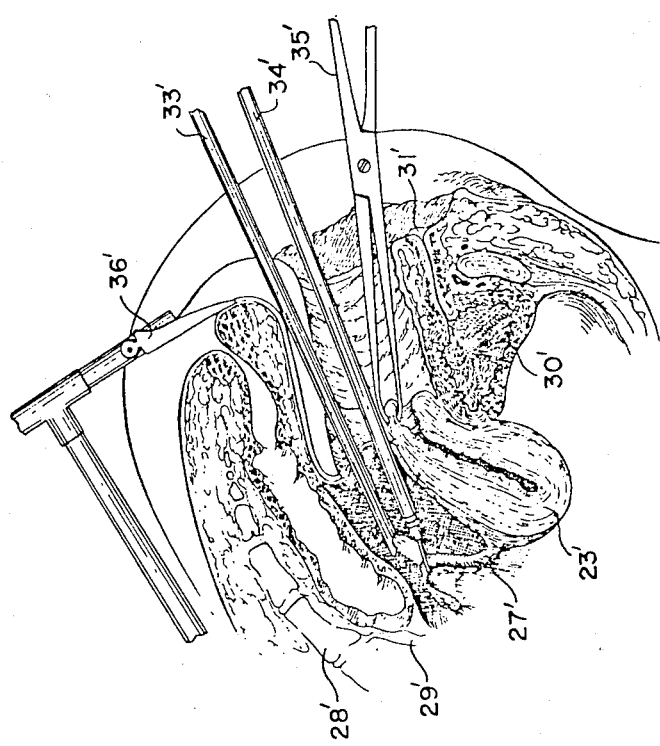
FIG. 33 shows the vaginal method of performing the ligation of the Fallopian tube wherein the ring applicator device and the culdoscope (light source) are used as two separate instruments.

FIG. 33 shows the vaginal approach utilized in the present invention wherein the ring applicator 34' which is used to grasp the Fallopian tube 27' is not physically combined with the culdoscope 33' (light source). The retractor 36' and the forceps 35'are utilized to assist the physician in performing the tubal ligation. In FIG. 33, 28' represents the spine of the patient, 29' is the rectum, 27' is the Fallopian tube, 23' is the uterus and 30' is the bladder.

Figure 34:
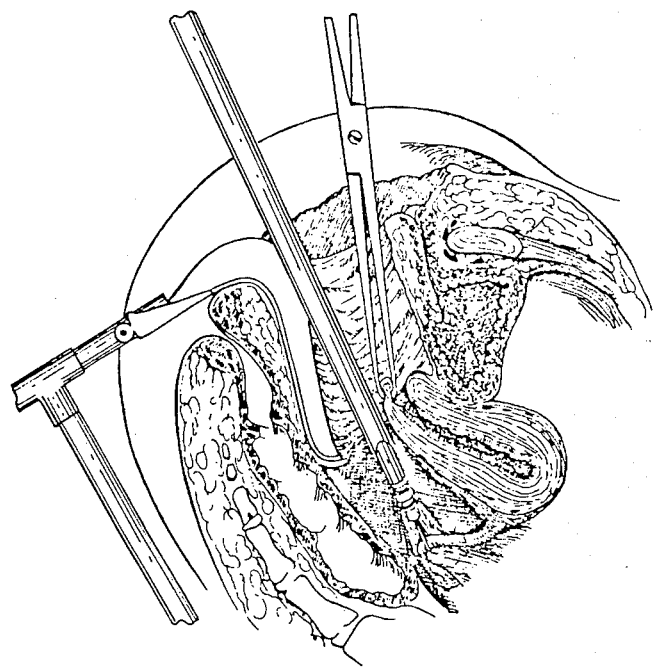
FIG. 34 shows the vaginal method similar to FIG. 32 wherein the laparoscope and ring applicator are combined into a single instrument.

FIG. 34 is similar to FIG. 33 with the exception that the ring applicator device is physically combined with the laparoscope as shown in FIG. 22.

The sterilization operation utilizing the ring applicator device as defined by the present invention renders sterilization so simple that only about 5 to 10 minutes are required to perform the operation and accordingly, an out-patient procedure may be employed where permitted. This is particularly important in developing countries where hospital facilities are not abundant and may not even be available.

A particular advantage of the present invention is that the blockage of the tubes can be made permanent or temporary, as desired. This particular feature of the invention depends upon the size and the elastic power of the rings employed. If the rings are very small and have a strong elastic power, they will so tightly grip the Fallopian tubes that the blood supply in this part of the tube will be completely blocked, thereby resulting in a sluffing off of the tubes to effect a permanent sterilization, analogous to the well known method of cutting and tieing the Fallopian tubes. However, if the elastic bands are of a larger size and have a smaller elastic power, it is possible to effect a temporary or reversible sterilization since, although the elastic band will serve to prevent the ovum passage to the uterus, the holding power thereof will not be so strong as to shut off the blood supply through the tubes. Accordingly, if the woman should desire to return to a normal situation at a later time, it would be possible for the Fallopian tubes to be restored to their natural function. Hence, the results of permanent or temporary sterilization are dependent upon the size of the rings used and the elastic power thereof.

The rings used for application to the Fallopian tubes are made of government-approved, non-tissue reactive material which have a strong enough elastic power to perform the function described herein. Various rubbery materials may, of course, be used. The preferred material is silicone rubber, for example, the material commercially available under the name "Silastic". Collagen or any other absorbable or nonabsorbable synthetic elastic material which is not harmful to human tissue may be employed, for example, latex rubber or Teflon (tetrafluoroethylene). As pointed out above, the size of the rings may be varied wherein smaller rings are used for permanent tubal ligation, and larger rings are used in connection with effecting a temporary sterilization. Spring-like metal rings, preferably made of stainless steel, can also be used, as discussed above.

The device of the present invention can be made of medically-approved materials, including many different types of metals, preferably stainless steel, plastics and the like and, hence, is relatively inexpensive because of its simple nature. It can also be made as a disposable instrument, for example, from a synthetic resin such as polyethylene, polypropylene, polycarbonate, polystyrene, polyamide, polyacetates, or acrylic resin. In this embodiment, the wall of the ring applicator can itself act as a laparoscope for transmitting the light from a light source to the internal cavity, and a tube can be disposed around the inner tube (which would have a needle-like point) to push an elastic ring over the salpinx portion of the Fallopian tube when it is slid or otherwise moved with respect to said inner tube. This embodiment of the invention would be especially attractive where inexpensive instruments are a necessity. Moreover, the ring applicator device of the present invention has a wide range of applicability since it can be used in conjunction with the regular abdominal laparoscopic technique, as discussed above, or in connection with the known vaginal culdascopic procedure. The use of the device eliminates the need for large, bulky equipment which is normally used with the electrical procedures employed in the prior art as well as the complicated carbon dioxide supply systems used with other techniques. A very simple and relatively small carbon dioxide supply system can be used together with the instrument, or a squeeze bulb may even be used to provide the necessary gas and to maintain the required gas pressure inside the abdominal cavity while the operation is being performed. The elimination of complicated electrical and gas supply systems makes it possible to save time in setting up for the procedure. In addition, as pointed out above, the operation may be carried out quite quickly in less than ten minutes.

It is to be understood that various specific mechanical embodiments may be employed to perform the various functions described herein. Basically, the invention comprises an instrument for puncturing and entering into the body cavity, grasping the Fallopian tubes, slipping an elastic ring thereover, and optionally cutting the tubes, if desired. The associated equipment represents technical modifications and adds to this basic idea, and a particularly preferred embodiment is the use of the ring applicator of the invention together with the laparoscope or a similar viewing instrument.

In an analogous manner, the method and device of the present invention may be used to effect the sterilization of the human male. In this case the appropriate incision is made and one or more elastic rings are applied to the vas to effect the ligature thereof and block the passage of the sperm. The elastic or stretchable rings used in this connection must, of course, be small enough to ligate the small diameter of the vas.

It is readily apparent that the device of the present invention can be used to occlude any anatomical tubular structure for any purpose.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of occluding a reproductive tubular member to effect at least temporary sterilization which comprises selecting a site in the wall of the abdominal cavity near said reproductive tubular member, surgically penetrating the wall of the abdominal cavity to provide an entry therein, inserting an elastic ring applicator device containing at least one elastic ring through said entry to the location area of said reproductive tubular member, reproductive said repproductive tubular member while viewing said area and withdrawing said reproductive tubular member sufficiently to form a bend therein and to block the same, effecting release of said elastic ring onto and around said bend in the reproductive tubular member in the bent position, releasing said reproductive tubular member from the ring applicator device to free the bent portion, and withdrawing said ring applicator device from the abdominal cavity thereby leaving an occluded reproductive tubular member therein.

2. The method of occluding a reproductive tubular member to effect at least temporary sterilization according to claim 1, wherein the elastic ring applicator device comprises an inner cylinder and an outer cylinder, said inner cylinder being coaxially and slidably disposed within said outer cylinder, the proximal end portion of said inner cylinder extending beyond the proximal end portion of the outer cylinder and containing at least one elastic ring disposed thereon and forceps means slidably disposed within said inner cylinder, and wherein the forceps means are displaced from the proximal end portion of the ring applicator device, a segment of the reproductive tubular member is grasped by said forceps means and pulled inside of the inner cylinder of the elastic ring applicator device a predetermined distance sufficient to form a bend in said reproductive tubular member, and the elastic ring is then displaced from the end of the inner cylinder to a position around the segment of the reproductive tubular member held by the forceps means thereof by axially moving the outer cylinder and the inner cylinder relative to each other, thereby forming a loop in said reproductive tubular member.

3. The method of claim 2, wherein a closed loop is formed in said reproductive tubular member, the ingress and egress to and from said loop being cut off by the elastic power of the elastic ring.

4. The method of occluding a reproductive tubular member to effect at leaast temporary sterilization according to claim 1, wherein the elastic ring applicator device comprises an inner cylinder and an outer cylinder, said inner cylinder being coaxially disposed within and in engaging relationship with said outer cylinder, the proximal end portion of said inner cylinder extending beyond the proximal end portion of the outer cylinder and containing at least one elastic ring disposed thereon, forceps means slidably disposed within said inner cylinder and means for rotating said outer and inner cylinders in the axial direction, and wherein the forceps means are displaced from the proximal end portion of the ring applicator device, a segment of the reproductive tubular member is grasped by said forceps means and pulled inside of the inner cylinder of the elastic ring applicator device a predetermined distance sufficient to form a bend in said reproductive tubular member and the elastic ring is then displaced from the end of the inner cylinder to a position around the segment of the reproductive tubular member held by the forceps means thereof by axially moving the outer cylinder and the inner cylinder relative to each other, thereby forming a loop in said reproductive tubular member.

5. The method of claim 4, wherein a closed loop is formed in said reproductive tubular member, the ingress and egress to and from said loop being cut off by the elastic power of the elastic ring.

6. The method of claim 1, wherein the reproductive tubular member is a Fallopian tube.

7. The method of claim 1, wherein the reproductibe tubular member is a vas deferens.

8. The method of claim 1, wherein the location area is inflated to obtain manipulation room.

9. The method of claim 1, wherein the reproductive tubular member is grasped at some intermediate point.

10. The method of claim 1, wherein optical viewing means and illuminating means are attached to the ring applicator device and a single incision is made in the abdominal wall to provide said entry into the abdominal cavity.

11. The method of claim 1, wherein optical viewing means and illuminating means are separate from the ring applicator device and an incision is made in the wall of the abdominal cavity for the optical viewing portion of said inner cylinder extending beyond the proximal end portion of the outer cylinder and containing at least one elastic ring disposed thereon and forceps means slidably disposed within said inner cylinder, and wherein the forceps means are displaced from the proximal end portion of the ring applicator device, a segment of the reproductive tubular member is grasped by said forceps means and pulled inside of the inner cylinder of the elastic ring applicator device a predetermined distance sufficient to form a bend in said reproductive tubular member, and the elastic ring is then displaced from the end of the inner cylinder to a position around the segment of the reproductive tubular member held by the forceps means thereof by axially moving the outer cylinder and the inner cylinder relative to each other, thereby forming a loop in said reproductive tubular member.

12. The method of claim 10, wherein the making an incision is made in the umbilicus.

13. The method of claim 11, wherein entry is obtained for the ring applicator device by making an incision in the umbilicus.

14. The method of claim 1, wherein the reproductive tubular member is withdrawn into the ring applicator device to form said bend therein.

15. The method of claim 14, wherein the elastic ring is disposed on the proximal end of the ring applicator device and is displaced therefrom around the bent portion of the reproductive.

16. The method of claim 2, wherein the location area is inflated with air or carbon dioxide gas to obtain manipulation room.

17. The method of claim 2, wherein the forceps means is provided with sharp edges and the loop in said reproductive tubular member is cut by said forceps means.

18. The method of claim 16, wherein a cannula having a trocar disposed therein is inserted into said entry and after the trocar is removed, the ring applicator is inserted into the space vacated by said trocar.

19. The method of claim 16, wherein a cannula housing two trocars is inserted into said entry and after the trocars are removed, the ring applicator device and an optical viewing means and illuminating are inserted into the spaces vacated by said trocars.

20. The method of claim 4, wherein the inner and outer cylinders are in screw engagement with each other and by rotating the outer cylinder the elastic ring is pushed from the proximal end portion of the inner cylinder to a position around the bent reproductive tubular member.

21. The method of claim 4, comprising a ring applicator, the proximal end of the inner cylinder having means thereon to selectively retain on its outer end surface at least two elastic occluding rings and said outer cylinder having an expandable end portion, wherein by axially moving the outer and inner cylinders relative to each other said expandable end portion cooperates with said proximal end portion of the inner cylinder for sequentially ejecting the elastic occluding rings from the inner cylinder after axially displacing the outer and inner cylinders relative to each other to position said expandable end portions behind a ring.

22. The method of claim 1, wherein said occluding method effects permanent sterilization.

23. A method of occluding a reproductive tubular member to effect at least temporary sterilization which comprises selecting a site in the wall of the abdominal cavity near said reproductive tubular member, surgically penetrating the wall of the abdominal cavity to provide an entry therein, inserting an elastic ring applicator device containing at least one elastic ring through said entry to the location area of said reproductive tubular member, grasping said reproductive tubular member while viewing said area and withdrawing said reproductive tubular member sufficiently to form a bend therein, effecting release of said elastic ring onto and around said bend in the reproductive tubular member to hold said tubular member in the bent position and to block the same, releasing said reproductive tubular member from the ring applicator device to free the bent portion, and withdrawing said ring applicator device from the abdominal cavity, thereby leaving an occluded reproductive tubular member therein.

* * * * *

UNITED STATES PATENT AND TRADEMARK OFFICE
CERTIFICATE OF CORRECTION

PATENT NO. : 3,989,049
DATED : November 2, 1976
INVENTOR(S) : InBae Yoon

It is certified that error appears in the above—identified patent and that said Letters Patent is hereby corrected as shown below:

col. 12, line 47 "reproductive said repproductive" deleted and --grasping said reproductive-- substituted therefor;

col. 13, line 18 "leaast" change to --least--;

line 28, before "in the axial direction" insert --relative to each other, thereby moving the outer cylinder--.

Signed and Sealed this

Twenty-eighth Day of October 1980

[SEAL]

Attest:

*Attesting Officer*

SIDNEY A. DIAMOND

*Commissioner of Patents and Trademarks*